(12) United States Patent
Kawahito

(10) Patent No.: US 8,066,962 B2
(45) Date of Patent: Nov. 29, 2011

(54) ENVIRONMENT HOLDING APPARATUS AND ENVIRONMENT CONTROL TYPE ANALYZER

(75) Inventor: Takashi Kawahito, Fujsawa (JP)

(73) Assignee: Nikon Corporation, Tokyo (JP)

( * ) Notice: Subject to any disclaimer, the term of this patent is extended or adjusted under 35 U.S.C. 154(b) by 1055 days.

(21) Appl. No.: 11/388,201

(22) Filed: Mar. 24, 2006

(65) Prior Publication Data

US 2006/0245976 A1    Nov. 2, 2006

Related U.S. Application Data

(63) Continuation of application No. PCT/JP2004/013539, filed on Sep. 16, 2004.

(30) Foreign Application Priority Data

Sep. 26, 2003    (JP)    .................... 2003-335630

(51) Int. Cl.
    *B01L 9/00*      (2006.01)
(52) U.S. Cl. .............. 422/565; 422/82.05; 422/567
(58) Field of Classification Search .............. 422/81, 422/82.05, 82.09, 99–104, 500, 561, 562, 422/563, 565, 567
See application file for complete search history.

(56) References Cited

U.S. PATENT DOCUMENTS

| | | | |
|---|---|---|---|
| 5,143,854 A | | 9/1992 | Pirrung et al. |
| 5,682,232 A | | 10/1997 | Tajima et al. |
| 6,264,891 B1 | * | 7/2001 | Heyneker et al. ............ 422/64 |
| 6,335,166 B1 | * | 1/2002 | Ammann et al. .............. 435/6 |
| 6,867,050 B2 | * | 3/2005 | Peck et al. ..................... 506/40 |
| 7,008,769 B2 | * | 3/2006 | Henderson et al. ............ 435/6 |
| 7,419,836 B2 | * | 9/2008 | Schuerf et al. ................ 436/164 |
| 2003/0008296 A1 | | 1/2003 | Hori et al. |
| 2003/0013184 A1 | | 1/2003 | Streit et al. |
| 2004/0229210 A1 | * | 11/2004 | Sabry et al. ................... 435/4 |
| 2005/0196325 A1 | | 9/2005 | Bathe et al. |

FOREIGN PATENT DOCUMENTS

| | | |
|---|---|---|
| JP | A-9-61341 | 3/1997 |
| JP | A-11-315095 | 11/1999 |
| JP | A-2001272404 | 10/2001 |
| JP | A-2002-542481 | 12/2002 |
| JP | A-2003-57237 | 2/2003 |
| WO | WO 90/15070 | 12/1990 |
| WO | WO 00/17643 | 3/2000 |

* cited by examiner

*Primary Examiner* — Jill Warden
*Assistant Examiner* — Dwayne K Handy
(74) *Attorney, Agent, or Firm* — Morgan, Lewis & Bockius LLP

(57) ABSTRACT

An environment holding apparatus includes: a first chamber that has an opening and holds a sample; a moving stage that is two-dimensionally moved with the first chamber being mounted thereon; and a first plane that includes an introduction port having a function of introducing gas adjusted to predetermined conditions into the first chamber from a pipe, and that is provided so as to cover the opening of the first chamber. The first plane is provided so as to be kept stationary regardless of a movement of the moving stage and the opening of the first chamber is two-dimensionally moved along the first plane by the movement of the moving stage.

13 Claims, 6 Drawing Sheets

ENVIRONMENT HOLDING APPARATUS AND ENVIRONMENT CONTROL TYPE ANALYZER

This application is a continuation of International Application No. PCT/JP2004/013539, with an international filing date of Sep. 16, 2004, which is hereby incorporated by reference. This application also claims the benefit of Japanese Patent Application No. 2003-335630, filed Sep. 26, 2003, which is hereby incorporated by reference.

BACKGROUND OF THE INVENTION

1. Field of the Invention

The present invention relates to an environment control type analyzer having functions of holding, observing, and analyzing a sample, particularly, a biological sample.

2. Description of Related Art

The marked development of biotechnology in recent years has led to an increased demand for a technique which enables a biological sample to be observed and analyzed in situ, and images thereof to be captured in situ. In general, the biological sample is maintained in a liquid containing components required for living, a so-called "culture medium", at a temperature around 37° C. Furthermore, the surroundings of the culture medium are maintained at a high humidity of almost 100% and with a carbon dioxide gas density of 5%. A system is known, which has a function of supplying an adjusted air flow at a predetermined temperature, a predetermined humidity, and a predetermined carbon dioxide gas density, into a sample chamber from the outside of the system.

SUMMARY OF THE INVENTION

With conventional systems, when observing a different position of a biological sample, a chamber where a microtitration plate is mounted is horizontally moved with an XY table. In this case, there is a need to maintain the humidity and the carbon dioxide gas density at predetermined values. This requires a piping system in which pipes are provided to the XY table for supplying air and carbon dioxide gas with an adjusted humidity. However, such a piping system has a problem of mechanical resistance to the movement of the XY table when the XY table is moved. Furthermore, in some cases, this can lead to a problem of damage of the pipes due to repeated pipe bending actions.

According to the 1st aspect of the invention, an environment holding apparatus comprises: a first chamber that has an opening and holds a sample; a moving stage that is two-dimensionally moved with the first chamber being mounted thereon; and a first plane that includes an introduction port having a function of introducing gas adjusted to predetermined conditions into the first chamber from a pipe, and that is provided so as to cover the opening of the first chamber. The first plane is provided so as to be kept stationary regardless of a movement of the moving stage; and the opening of the first chamber is two-dimensionally moved along the first plane by the movement of the moving stage.

According to the 2nd aspect of the invention, in the environment holding apparatus according to the 1st aspect, it is preferred that the end of the wall of the first chamber forming the opening is positioned adjacent to the first plane.

According to the 3rd aspect of the invention, in the environment holding apparatus according to the 1st aspect, it is preferred that the moving stage is moved within a range where the introduction port of the first plane is positioned within the opening.

According to the 4th aspect of the invention, in the environment holding apparatus according to the 1st aspect, it is preferred that the predetermined conditions of the gas include at least one of temperature, humidity, and composition.

According to the 5th aspect of the invention, in the environment holding apparatus according to the 4th aspect, it is preferred that the composition of the gas includes air and carbon dioxide gas.

According to the 6th aspect of the invention, in the environment holding apparatus according to the 1st aspect, it is preferred that the first plane includes an opening/shutting unit that enables the first plane to be partially opened and shut.

According to the 7th aspect of the invention, in the environment holding apparatus according to the 6th aspect, it is preferred that the opening/shutting unit enables switching between a first state in which the first chamber is exposed to an external space through an opening and a second state in which the opening is closed.

According to the 8th aspect of the invention, in the environment holding apparatus according to the 6th aspect, it is preferred that the opening/shutting unit enables switching between a first state in which the first chamber is exposed to the external space through an opening, a second state in which the opening is closed, and a third state in which illumination light is introduced into the first chamber through a transparent window member.

According to the 9th aspect of the invention, in the environment holding apparatus according to the 1st aspect, it is preferred that: there is further provided a second chamber that stores the first chamber and the moving stage; and the first plane is one of planes forming an exterior of the second chamber.

According to the 10th aspect of the invention, in the environment holding apparatus according to the 9th aspect, it is preferred that: the first chamber includes a first opening and a shutter having a function of opening/shutting the first opening; and the second chamber includes a second opening and a shutter, which has a function of opening/shutting the second opening, at a position facing the first opening.

According to the 11th aspect of the invention, an environment control type analyzer comprises: an environment holding apparatus according to the 1st aspect; an analyzer that analyzes a sample held within the first chamber; and an environment adjustment apparatus that is connected to the first chamber through the pipe and the first plane to maintain the inside of the first chamber under a predetermined environment.

According to the 12th aspect of the invention, an environment control type analyzer comprises: an environment holding apparatus according to the 8th aspect; an analyzer that analyzes a sample held within the first chamber; a transmitted illumination device that is provided to face a detecting unit of the analyzer with the sample put therebetween, and that illuminates the sample through the window member; and an environment adjustment apparatus that is connected to the first chamber through the pipe and the first plane to maintain the inside of the first chamber under a predetermined environment.

According to the 13th aspect of the invention, an environment control type analyzer comprises: an environment holding apparatus according to the 13th aspect; an analyzer at least a part of which is disposed within the second chamber, and that analyzes a sample held within the first chamber; and an environment adjustment apparatus that is connected to the first chamber through the pipe and the first plane to maintain the inside of the first chamber under a predetermined environment.

According to the 14th aspect of the invention, in the environment control type analyzer according to the 13th aspect, it is preferred that there is further provided a dehumidifier that dehumidifies the inside of the second chamber.

According to the 15th aspect of the invention, an environment holding apparatus comprises: a first chamber that has an opening and holds a sample; a moving stage that is two-dimensionally moved with the first chamber being mounted thereon; and a first plane that is provided so as to cover the opening of the first chamber. The first plane is provided so as to be kept stationary regardless of a movement of the moving stage; and the opening of the first chamber is two-dimensionally moved along the first plane by the movement of the moving stage.

According to the 16th aspect of the invention, in the environment holding apparatus according to the 15th aspect, it is preferred that: there is further provided a second chamber that stores the first chamber and the moving stage; the first plane is one of planes forming an exterior of the second chamber; and an end of a wall of the first chamber forming the opening is positioned adjacent to the first plane.

DESCRIPTION OF PREFERRED
EMBODIMENT(S)

Description will be made below regarding an environment holding apparatus (environment holding chamber) according to the present invention, and an environment control type analyzer employing the environment holding apparatus with reference to the drawings.

Figure 1:
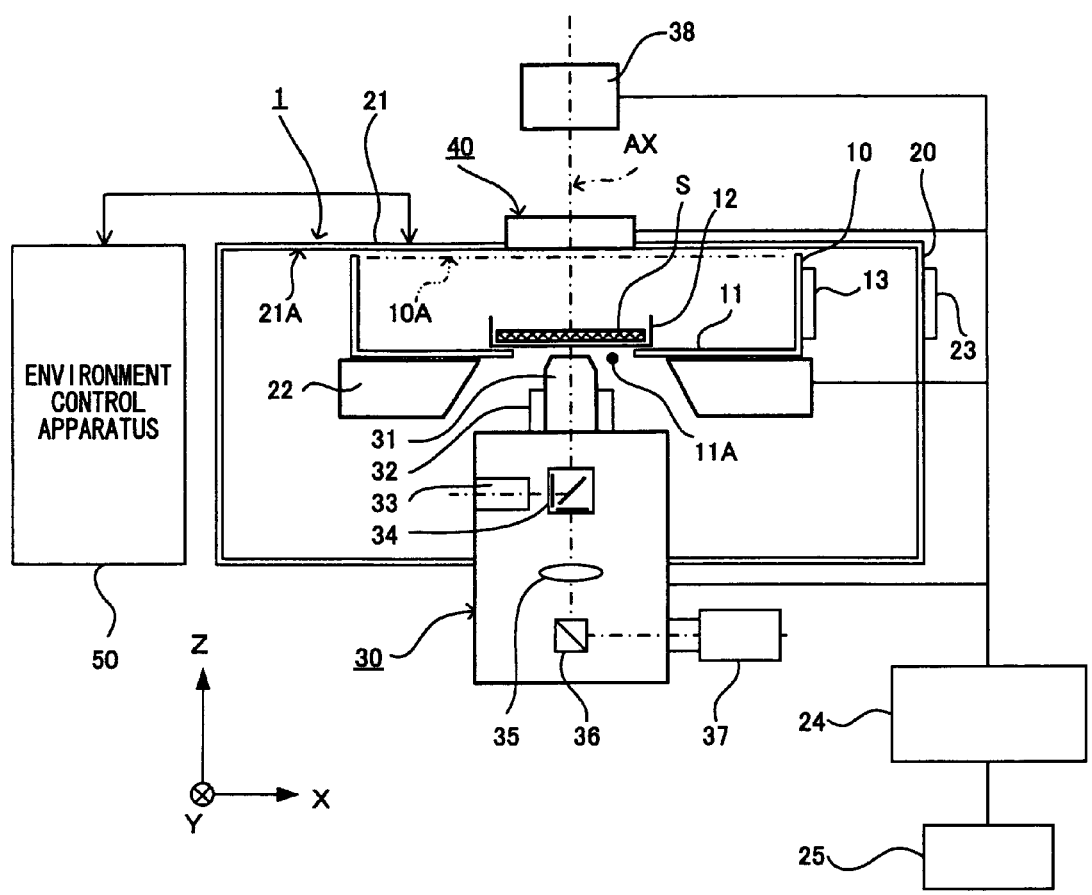
FIG. 1 is a schematic configuration diagram which shows a configuration of an environment holding apparatus according to an embodiment of the present invention.
Figure 2:
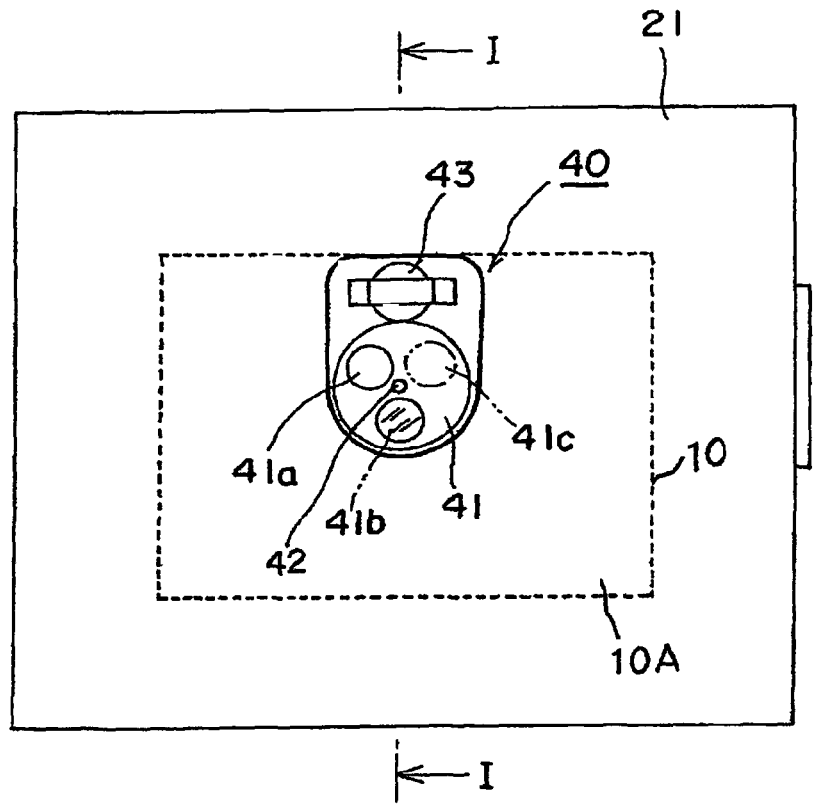
FIG. 2 is a top view of the environment holding apparatus according to the embodiment of the present invention.
Figure 3:
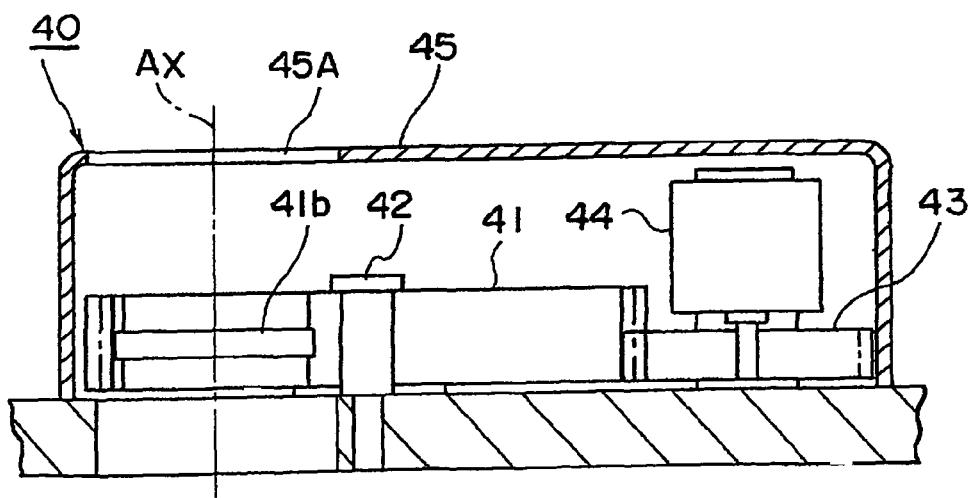
FIG. 3 is a cross-sectional view taken along line I-I in FIG. 2, and is a diagram which shows a configuration of a shutter mechanism.
Figure 4:
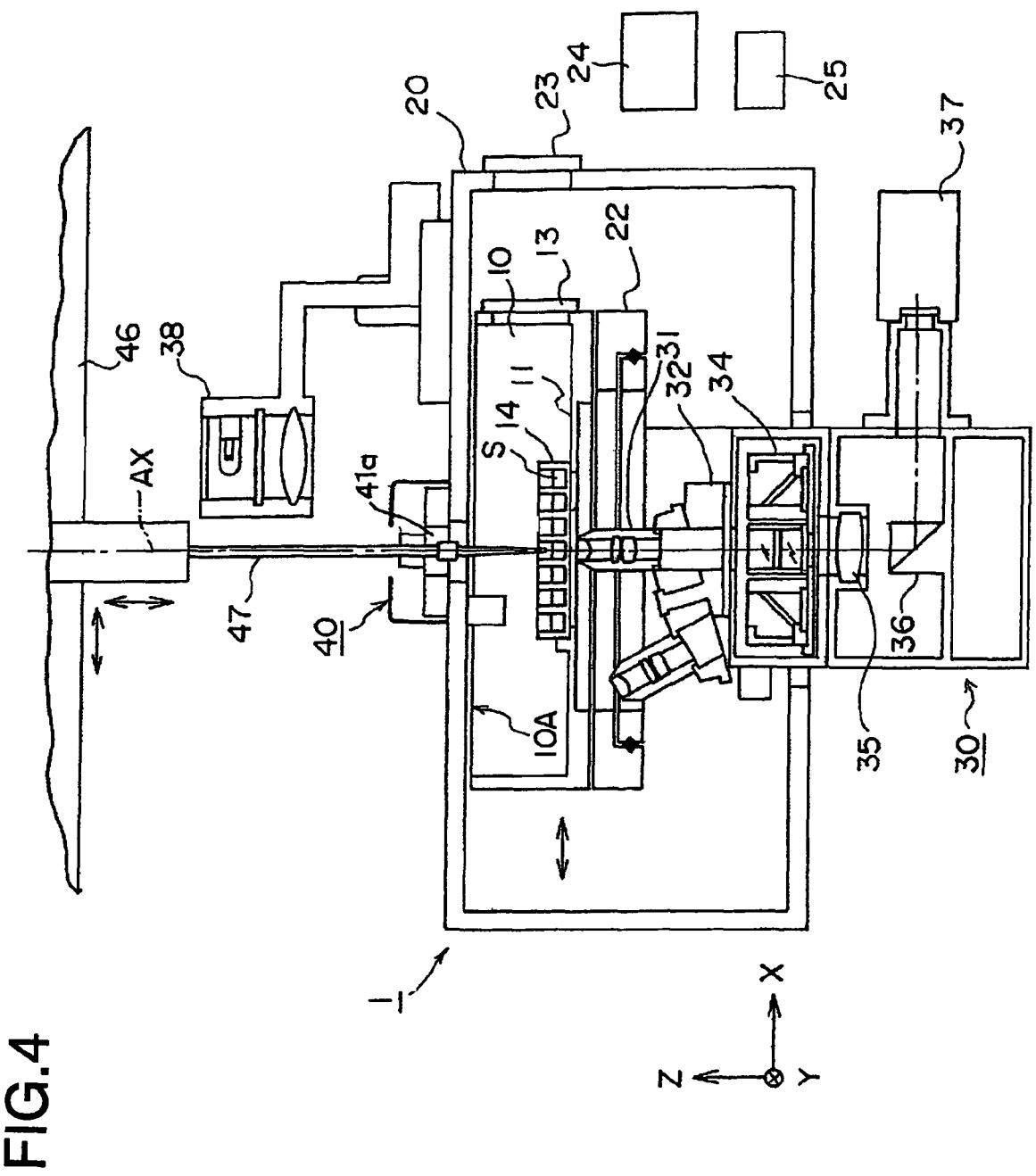
FIG. 4 is a configuration diagram for describing the operation of the environment holding apparatus according to the embodiment of the present invention.

FIG. 1 is a schematic configuration diagram which shows a configuration of an environment control type analyzer according to the present embodiment. FIG. 2 is a top view of the environment control type analyzer according to the present embodiment. FIG. 3 is a cross-sectional view taken along line I-I in FIG. 2, and is a diagram which shows a configuration of a shutter mechanism. FIG. 4 is a configuration diagram for describing the operation of the environment control type analyzer according to the present embodiment. The same components shown in FIGS. 1 through 4 are denoted by the same reference numerals. Note that the directions are represented in the XYZ-rectangular coordinate system for convenience of explanation, as shown in the drawings.

An environment control type analyzer according to the present embodiment includes: an environment holding apparatus 1 for maintaining a predetermined environment where a sample is placed; a microscope 30 for analyzing the sample; an environment control (adjustment) device 50 for controlling the environment in the environment holding apparatus 1; and a control unit 24 and a PC 25 for controlling these components. In particular, the feature of the present invention is that the environment control type analyzer includes the aforementioned environment holding apparatus 1.

Referring to FIG. 1, the environment holding apparatus 1 according to the present embodiment has a configuration in which a sample chamber 10, which is a first chamber, is stored in an airtight container 20 which is a second chamber. The environment in the sample chamber 10 is maintained under predetermined conditions by the environment control apparatus 50. Description will be made later regarding the environment control apparatus 50 with reference to FIGS. 5 and 6.

The sample chamber 10 has an open top face, i.e., an open face 10A. Furthermore the sample chamber 10 has an opening in a base plate 11. A culture medium container 12 for holding a biological sample S is mounted on the base plate 11 so as to close the opening 11A. The sample chamber 10 is mounted on an XY moving stage 22, which enables the sample chamber 10 to be moved in the X and Y directions along the horizontal plane. Furthermore, an opening/shutting window 13 is provided on the side face of the sample chamber 10. This allows the culture medium container 12 to be put in and out, and enables maintenance of the inside of the sample chamber.

The airtight container 20 is a container for storing the sample chamber 10, the XY moving stage 22, and a part of the microscope 30 which is an analysis device. The open face 10A of the sample chamber 10 is provided adjacent to and in parallel with a lower face 21A of an upper plate 21 which is one of walls forming the exterior of the airtight container 20. Such an arrangement enables the sample chamber 10 to be moved in the X and Y directions along the horizontal plane while maintaining the condition that the open face 10A of the sample chamber 10 is positioned adjacent to and in parallel with the lower face 21A of the upper plate 21 of the airtight container 20. That is to say, such an arrangement enables the sample chamber 10 to be horizontally moved while maintaining the condition that the end of each side wall (side plate 15 and so forth in FIG. 5) of the sample chamber 10 forming the open face 10A is positioned adjacent to the lower face 21A of the upper plate 21 of the airtight container 20. Also, the upper plate 21 of the airtight container 20 covers the open face 10A.

With such an arrangement, the upper plate 21 of the airtight container 20 almost completely closes the open face 10A of the sample chamber 10. This maintains the airtightness of the inside of the sample chamber 10 and the inside of the airtight container 20, independent of one another at all times. The airtight container 20 is fixed to the microscope 30. This allows the sample chamber 10 to be moved in the X and Y directions with the XY moving stage 22 while keeping the airtight container 20 stationary. That is to say, the upper plate 21 is provided so as to be kept stationary, regardless of the movement of the XY moving stage 22. On the other hand, an opening/shutting window 23 is provided on the side face of the airtight container 20. This allows the culture medium container 12 to be put in and out, and enables maintenance of the insides of the sample chamber and airtight container. The upper plate 21 includes a shutter mechanism 40 described later.

The microscope 30 includes an objective lens 31, a focusing device 32, an excitation light illumination device 33, a fluorescence filter arrangement 34, a second objective lens 35, a reflecting prism 36, an image capturing device 37, and a transmitted illumination device 38. The objective lens 31 is held by the focusing device 32, and can be moved in the direction along the optical axis AX, i.e., the Z direction. The transmitted illumination device 38 is disposed above the airtight container 20.

The control unit 24 is electrically connected to the microscope 30, the shutter mechanism 40, and the XY moving stage 22 via wiring. Furthermore, the control unit 24 is connected to the personal computer (PC) 25. The control unit 24 acquires various kinds of data with respect to the observation conditions, image capturing conditions, stage moving conditions, and so forth, from the PC 25, and outputs the data thus acquired to the microscope 30, the shutter mechanism 40, which is opening/shutting means, and the XY moving stage 22, as control signals. Furthermore, the control unit 24 outputs various kinds of control data and image data to the PC 25.

The shutter mechanism 40 includes a disk-shaped wheel 41, a rotational shaft 42, a gear 43, an electric motor 44, and a cover 45, as shown in FIGS. 2 and 3. The wheel 41 is mounted to the rotational shaft 42. The gear 43 is mounted to the rotational shaft of the electric motor 44. The wheel 41 and the gear 43 mesh with each other. The wheel 41 includes an opening 41a for introducing a biological sample into the first chamber, and a transparent plate 41b which is a transparent window member for introducing illumination light into the first chamber. A region 41c indicated by the imaginary line is a shielding region having neither opening nor transparent plate.

Furthermore, the wheel 41, the rotational shaft 42, the gear 43, and the electric motor 44 are covered with a cover 45 having an opening 45A formed therein. The wheel 41 can be switched between: a first position where the first chamber is exposed to the external space through the opening 41a; a second position where the opening 41a is closed; and a third position where illumination light is introduced into the first chamber through the transparent window member 41b. That is to say, the shutter mechanism 40 can be switched between: a first state in which the first chamber is exposed to the external space through the opening 41a; a second state in which the opening 41a is closed; and a third state in which illumination light is introduced into the first chamber through the transparent window member 41b.

Description will be made below regarding a method of use of the environment holding apparatus according to the present embodiment with reference to FIG. 4. Note that electrical wiring for connecting the control unit 24 and the PC 25, which is shown in FIG. 1, is not shown in FIG. 4.

First, a specimen well plate 14 (corresponding to the culture medium container 12 in FIG. 1) is set in the sample chamber 10 through the opening/shutting window 23 and the opening/shutting window 13 in order. Each of the opening/shutting window 23 and the opening/shutting window 13 has a configuration in which a shutter is provided to an opening. The well plate 14 is a transparent container having a structure in which multiple wells are arrayed. The electric motor 44 provided to the shutter mechanism 44 is rotationally driven according to a signal from the control unit 24. This rotates the gear 43, and the rotational force thereof turns the wheel 41 such that the center of the opening 41a is positioned on the optical axis AX. At this time, the inside of the sample chamber 10 is exposed to the external space. In this state, a pipette 47 of an injector 46 is inserted into the opening 41a, and the tip of the pipette 47 reaches the sample chamber 10.

The injector 46 can be moved in the X, Y, and Z directions by an unshown driving mechanism according to a signal from the control unit 24. Furthermore, the injector 46 has a mechanism which enables a culture solution containing a biological sample and a reaction reagent to be injected to each well of the well plate 14 through the pipette 47. When a biological sample or a reagent is divided and injected to each of the wells, the well plate 14 is moved in the X and Y directions with the XY moving stage 22. Note that at the time of injection, the transmitted illumination device 38 is removed from the optical axis AX as shown in the drawing.

Upon completion of injection of the culture solution or the like, the pipette 47 of the injector 46 is retracted upward. Then, the shutter mechanism 40 operates according to a signal from the control unit 24, and the transparent plate 41b or the shielding region 41c is positioned on the optical axis AX. In a case of transmitted image observation, the transparent plate 41b is positioned on the optical axis AX. In a case of fluorescence image observation, the shielding region 41c is positioned on the optical axis AX. At this time, the inside of the sample chamber 10 is closed to both the airtight container 20 and the external space.

The inside of the sample chamber 10 is kept in this state at a predetermined temperature, humidity, and gas density, whereupon analysis is started.

Next, description will be made regarding microscopic observation using the environment holding apparatus according to the present embodiment. In a case of the transmitted image observation, the transmitted illumination device 38 is returned to a position on the optical axis AX. Then, the biological sample S is irradiated with illumination light. The light, which has passed through the biological sample S, is introduced to the objective lens 31 through the well plate 14. The light thus introduced to the objective lens 31 passes through the fluorescence filter arrangement 34 and the second objective lens 35, is reflected by the reflecting prism 36, and forms an image on an image sensor of the image capturing device 37.

At the microscope 30, the observation conditions such as adjustment of the luminance of the illumination light source, switching between various kinds of filters, switching of the observation magnification, adjustment of a field diaphragm, and so forth, are set according to control signals from the control unit 24. At the image capturing device 37, the image capturing conditions such as the gain of a CCD, shutter speed, numerical aperture, and so forth, and image capturing timing synchronous with the illumination device, are set according to control signals from the control unit 24.

The microscopic image data of the biological sample S is transmitted to the PC 25 through the control unit 24, and is displayed on a monitor as a microscopic image. Also, the PC 25 has a function of performing image processing for the microscopic image and displaying the microscopic image thus subjected to image processing on the monitor. Also, the PC 25 has a function of displaying the control data such as the aforementioned observation conditions, image capturing conditions, and so forth, on the monitor as necessary.

Before observation of a biological sample S injected to a different well, the well plate 14 is moved in the X and Y directions with the XY moving stage 22 according to a control signal from the control unit 24. In a case that the focal position is deviated due to the movement of the well plate 14 or the switching of the observation magnification, the objective lens 31 is moved in the Z direction by the focusing device 32. This operation enables the focal position to be adjusted for the biological sample S. Also, the control data such as the moving conditions of the stage and so forth can be displayed on the monitor of the PC 25 as necessary. For example, the information regarding the distance between the XY moving stage 22 and the base position may be displayed. This facilitates identification of the biological sample S injected to each of the wells.

In a case of fluorescence image observation, the light from the excitation light illumination device 33 passes through a light modulation filter (not shown) and the fluorescence filter arrangement 34, and is introduced from below the objective lens 31. The light introduced to the objective lens 31 is cast onto the biological sample S containing a fluorescent material through the well plate 14. Upon irradiating the biological sample S with the excitation light, the biological sample S emits fluorescence. The fluorescence passes through the well plate 14, the objective lens 31, the fluorescence filter arrangement 34, and the second objective lens 35, is reflected by the reflecting prism 36, and forms an image on the image sensor of the image capturing device 37. With regard to the microscopic observation, image data processing, stage moving, and so forth, for the fluorescence image observation, generally the same operations are performed as with the transmitted image observation.

Figure 5:
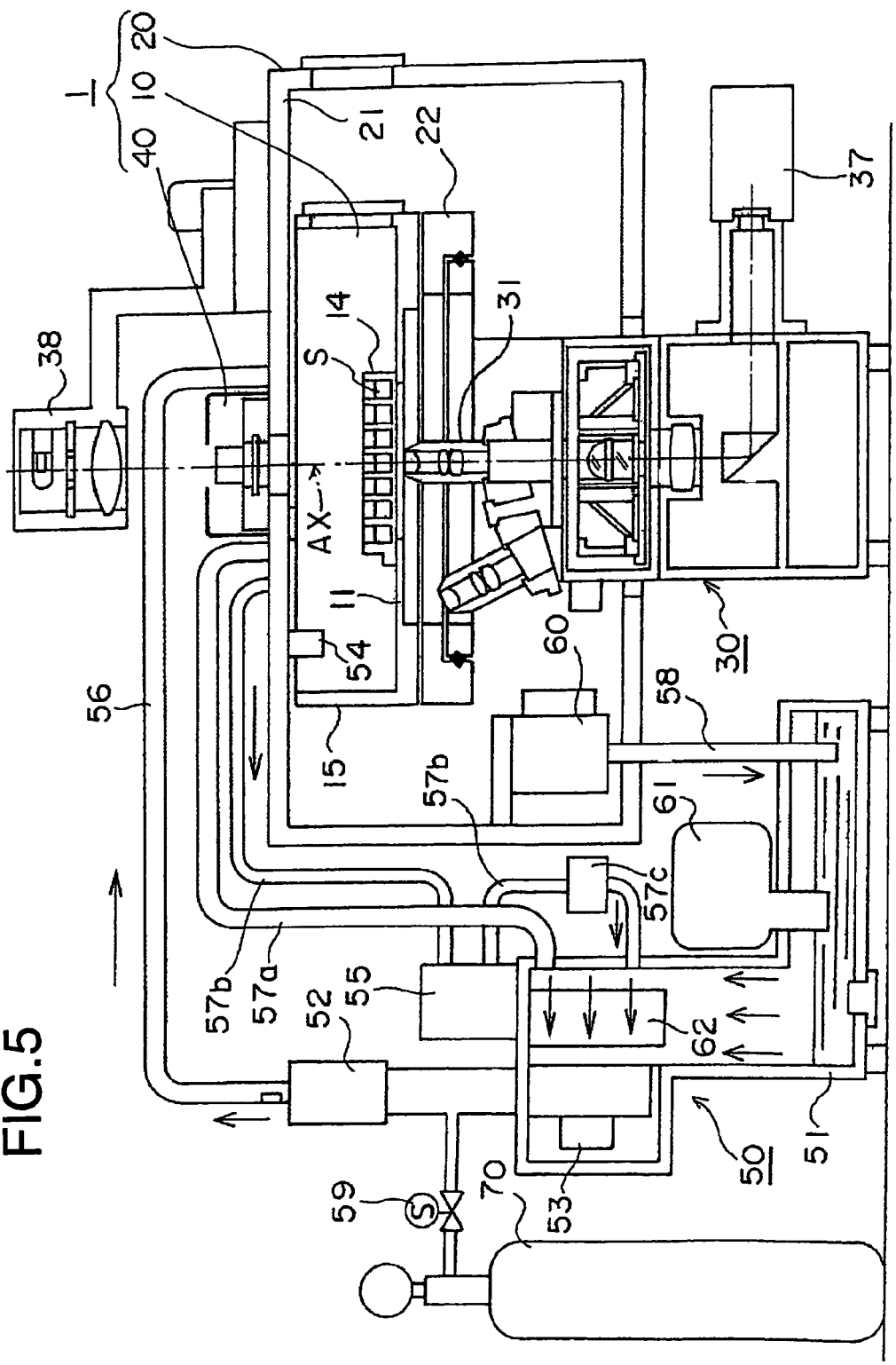
FIG. 5 is a schematic configuration diagram which shows an overall configuration of an environment control type analyzer according to an embodiment of the present invention, with the sample chamber being set to the base position.
Figure 6:
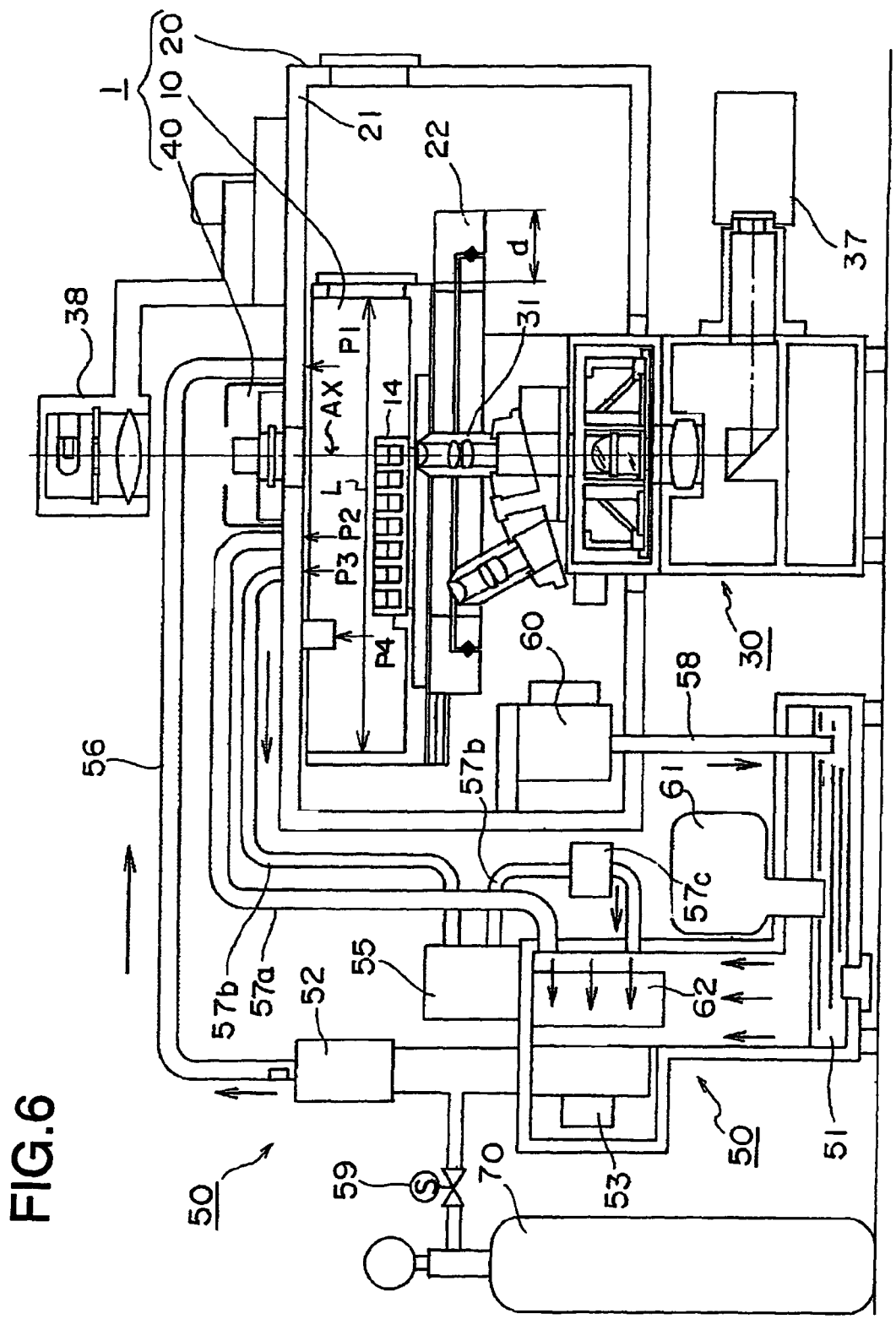
FIG. 6 is a schematic configuration diagram which shows the overall configuration of the environment control type analyzer with the sample chamber shifted from base position.

Description will be made regarding an environment adjustment method for the inside of the sample chamber 10. FIG. 5 is a schematic configuration diagram which shows an overall configuration of an environment control type analyzer comprising the environment holding apparatus 1, the environment control apparatus 50, and the microscope 30 shown in FIG. 1, with the sample chamber being set to the base position. FIG. 6 is a schematic configuration diagram which shows the overall configuration of the environment control type analyzer with the sample chamber shifted from base position. Both FIGS. 5 and 6 show an arrangement in which the environment control apparatus 50 is connected to the environment holding apparatus 1 shown in FIG. 1. The same components shown in FIGS. 5 and 6 as those shown in FIGS. 1 through 4 are denoted by the same reference numerals, and description thereof will be omitted. Also, the control unit 24 and the PC 25 are not shown in these drawings.

The environment control apparatus 50 is an apparatus which generates a gas at a desired temperature, humidity, and composition, and which circulates the gas thus generated in the sample chamber 10. That is to say, the gas, in which the conditions have been set to predetermined values, is transmitted into the sample chamber 10. The environment control apparatus 50 includes a humidifier 51, a heater 52, a blower 53, a temperature/humidity sensor 54, a $CO_2$ gas sensor 55, a reserve tank 61, and a cooler 62.

The heater 52 is connected to the upper plate 21 of the airtight container 20 through a gas transmission tube 56 by piping. A tube can be referred to as a pipe. The cooler 62 is disposed within the humidifier 51, and is connected to the upper plate 21 of the airtight container 20 through a gas inlet tube 57a and a gas inlet tube 57b by piping. The $CO_2$ gas sensor 55 is provided at a position on the path of the gas inlet tube 57b. The piping connection portion of the upper plate 21 communicates with the sample chamber 10. The humidifier 51 is connected to a dehumidifier 60 through a drain tube 58 by piping. A solenoid valve 59 is provided to the path branched from the path between the heater 52 and the blower 53, which enables gas to be introduced from a $CO_2$ gas cylinder 70.

The temperature/humidity sensor 54 is fixed on the lower face of the upper plate 21 of the airtight container 20. The $CO_2$ gas sensor 55 is fixed at a certain position on the path of the gas inlet tube 57b for monitoring $CO_2$ gas density in the sample chamber 10. Each of these tubes is thermally insulated.

Before supplying the gas to the sample chamber 10 through the gas transmission tube 56, the composition, humidity, and temperature of the gas are adjusted as follows. The gas composition is adjusted by controlling the opening amount of the solenoid valve 59 according to the feedback of the measurement value of the $CO_2$ gas sensor 55. The humidity is adjusted by controlling the driving voltage applied to an ultrasonic atomizer device included in the humidifier 51 according to the feedback of the measurement value of the temperature/humidity sensor 54. The ultrasonic atomizer device performs ultrasonic vibration of the water stored in the humidifier 51 so as to generate water vapor. Note that the reserve tank 61 supplies water to the humidifier 51 so as to maintain a predetermined amount of water stored in the humidifier 51. The temperature is adjusted by controlling the current applied to an electric heater of the heater 52 according to the feedback of the measurement value of the temperature/humidity sensor 54. Also, the temperature of the gas, which is supplied to the sample chamber 10, may be adjusted using both the heater 52 and the cooler 62.

The gas thus adjusted to a temperature of 37° C., a humidity (RH) of 100%, and a $CO_2$ density of 5%, for example, is supplied to the sample chamber 10 from the environment control apparatus 50 through the gas transmission tube 56. The gas thus supplied is returned to the environment control apparatus 50 from the sample chamber 10 through the gas inlet tubes 57a and 57b. Besides the gas circulating through the circulating path, an extremely small amount of the adjusted gas leaks from the gap between the upper plate 21 of the airtight container 20 and the side plate 15 of the sample chamber 10 and the gap between the well plate 14 and a base plate 11 of the sample chamber 10. The adjusted gas which has leaked is subjected to water separation by the dehumidifier 60, and the water thus separated is discharged to the humidifier 51. Such an arrangement maintains a dry environment in the airtight container 20 at a temperature 37° C., and a $CO_2$ density of 5%, for example. A peltier device may be employed in the dehumidifier 60. Also, an simple arrangement may be made in which silica gel is employed in the dehumidifier 60.

The adjusted gas circulating through the circulating path is introduced into the sample chamber 10 again by the environment control device 50 while maintaining a predetermined temperature, humidity, and gas composition thereof. This enables the biological sample S to be observed and analyzed while maintaining the environment of the inside of the sample chamber 10 under predetermined conditions at all times. The sample chamber 10 is stored in the airtight container 20, thereby preventing the adjusted gas from leaking to the outside.

Next, description will be made regarding the environment control type analyzer according to the present embodiment, with the sample camber 10 shifted from the base position, with reference to FIG. 6. In FIG. 6, with the optical axis AX as the base position, the sample chamber 10 is positioned shifted to the left side from the optical axis AX by the distance d.

The length of the sample chamber 10 is represented by L. The fixed positions of the gas transmission tube 56, the gas inlet tube 57a, the gas inlet tube 57b, and the temperature/humidity sensor 54 are represented by P1, P2, P3, and P4, respectively. In this case, all the fixed positions P1, P2, P3, and P4 are within a range of the length L. That is to say, the sample chamber 10 is moved while maintaining the fixed positions P1, P2, P3, and P4 within the open face 10A (FIG. 1) of the sample chamber 10.

As described above, the circulating path for circulating the adjusted gas is kept stationary regardless of the displacement and movement of the sample chamber 10 from the base position. This maintains the environment of the inside of the sample chamber 10 under predetermined conditions at all times, thereby enabling stable observation and analysis of the biological sample S for a long time. Furthermore, with the apparatus according to the present embodiment, while only the sample chamber 10 within the airtight container 20 is a moving component, the wiring of the XY stage 22 and the shutter mechanism 40 is kept stationary. The tubes and pipes also do not move. This eliminates the risk of breaking of the wiring, and eliminates the disadvantage of driving resistance on the driving device due to the piping and the wiring.

In some case, at the time of observing the biological sample, an additional reagent or culture solution is supplied to the sample. Such supply of the additional reagent or culture solution is performed using the injector 46 and the pipette 47. Also, at the time of microscopic observation, there is a need to provide the transparent window for introducing illumination light. In particular, at the time of injection of the reagent or the like using the injector 46 and the pipette 47, the inside of the sample chamber 10 communicates with the outside air. Accordingly, the opening is preferably formed with a small size. With the aforementioned arrangement according to the present embodiment, the upper plate 21 of second chamber 20 is positioned near the open face 10A of the first chamber 10. Such an arrangement enables a reagent or the like to be injected to each of wells by having a single opening for injection on the upper plate 21 and moving the first chamber 10. That is to say, such an arrangement enables a reagent or the like to be supplied to a sample with a large width without providing a particularly large opening corresponding to such a sample with a large width.

Description will be made below regarding modifications of the present embodiment. Description has been made in the present embodiment regarding an arrangement in which the microscope 30 is employed as an analyzer. Also, an arrangement may be made in which a photosensor is employed instead of the microscope. Such an arrangement enables the intensity and saturation of the fluorescence emitted from the biological sample S to be measured. Also, various types of analyzers may be employed. That is to say, the present invention may be applied to various types of analyzers having a function of analyzing a sample while maintaining a predetermined environment for the sample.

Also, the entire components of the analyzer may be stored in the airtight container 20. Also, a part of the analyzer may be stored in the airtight container 20. For example, the optical components from the objective lens 31 to the fluorescence filter arrangement 34 of the microscope 30 may be stored within the airtight container 20. Such an arrangement enables the internal volume of the airtight container 20 to be reduced, thereby enabling a compact-size airtight container 20 to be designed.

Figure 7:
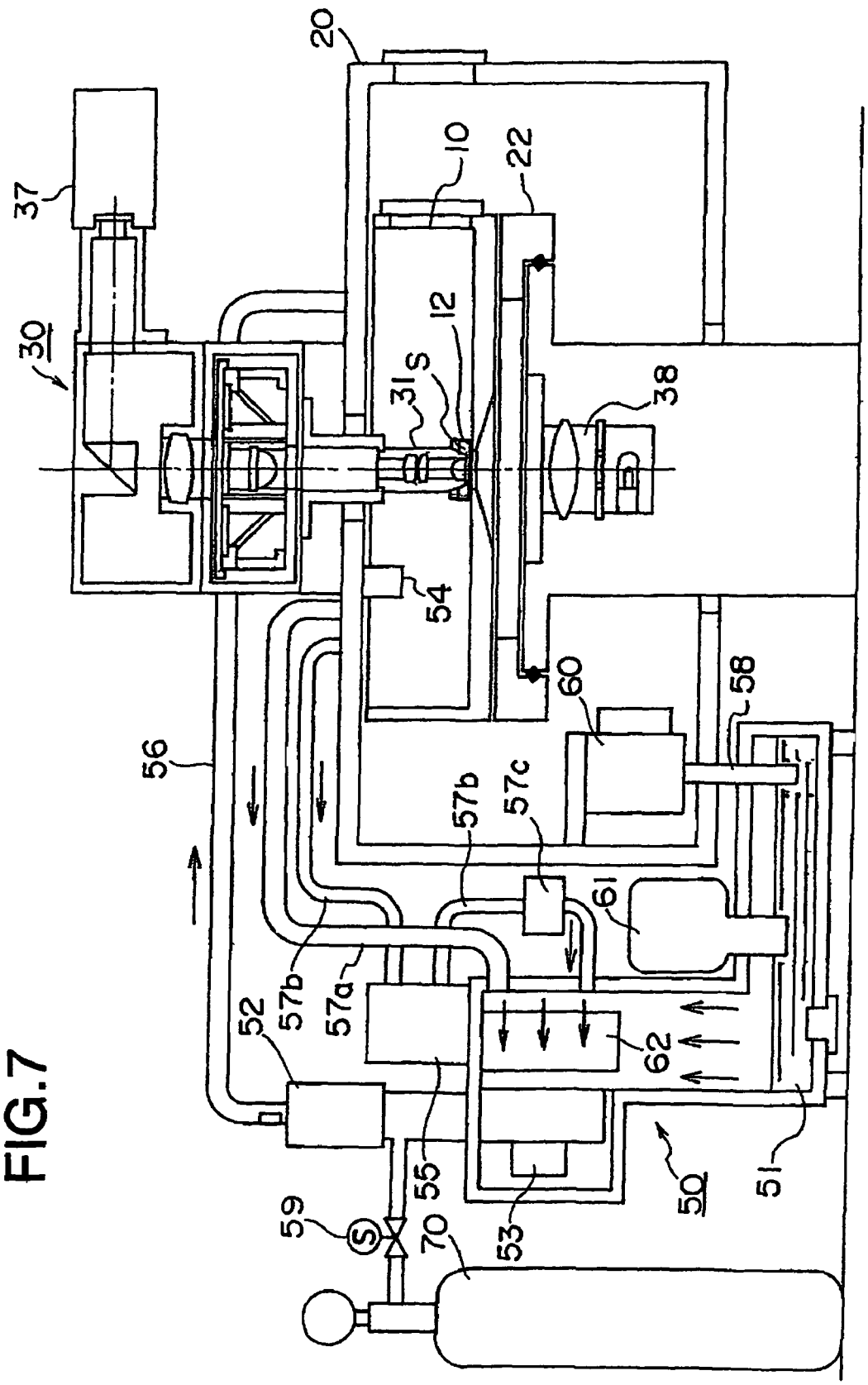
FIG. 7 is a schematic configuration diagram which shows an overall configuration of an environment control type analyzer employing an upright microscope, which is an modification of the embodiment of the present invention.

Also, an arrangement may be made employing an upright microscope as shown in FIG. 7, instead of the inverted microscope employed in the present embodiment. The same components shown in FIG. 7 as those shown in FIG. 5 are denoted by the same reference numerals. With such an arrangement shown in FIG. 7, the optical components from the objective lens 31 through the image capturing device 37 are disposed above the airtight container 20, and the transmitted illumination device 38 is disposed underneath the sample chamber 10.

The lens barrel of the objective lens 31 is inserted into the upper plate of the airtight container 20 through a sealing member. The sample chamber 10 can be moved in the X and Y directions with the XY moving stage 22. In a case that the transmitted image observation is not performed, the light source of the transmitted illumination device 38 is turned off. Such an arrangement employing the upright microscope enables the biological sample S to be directly observed, rather than through the culture container and the base of the well plate.

As described above, the environment holding apparatus has a configuration in which an introduction port of the pipe, which introduces a gas with a controlled temperature, humidity, and carbon dioxide gas density into the first chamber 10, is provided at a fixed portion (on the plane (upper plate 21) of the second chamber 20 adjacent to the first chamber), thereby controlling the environment of the inside of the first chamber 21. In order to observe the sample while keeping the microscope or the analyzer at the same temperature as that of the sample within the first chamber 10, the temperature of the second chamber 20 is preferably maintained at the same temperature as that in the first chamber 10. Description has been made in the aforementioned embodiment regarding an arrangement in which the airtight container 20 is employed as the second chamber. The present invention is not restricted to such an arrangement in which the second chamber 20 has an airtight structure. Also, the second chamber may be formed without an airtight structure, as long as the second chamber has a structure which enables the temperature to be controlled. On the other hand, in order to prevent the adjusted gas from leaking to the surroundings outside of the second chamber 20, the second chamber 20 preferably has an airtight structure.

While description has been made regarding various embodiments and modifications, the present invention is not restricted to the contents thereof. Rather various modifications of the present invention may be made, which are also encompassed in the technical scope of the present invention.

What is claimed is:

1. An environment holding apparatus comprising:
a first chamber that has an opening and holds a sample;
a moving stage that is two-dimensionally moved with the first chamber being mounted thereon; and
a first plane that includes an introduction port having a function of introducing gas adjusted to predetermined conditions into the first chamber from a pipe, and that is provided so as to cover the opening of the first chamber, wherein:
the first plane is provided so as to be kept stationary regardless of a movement of the moving stage; and
the opening of the first chamber is two-dimensionally moved along the first plane by the movement of the moving stage and the end of the wall of the first chamber forming the opening of the first chamber is positioned adjacent to the first plane, so that the opening of the first chamber is moved while being closed by the first plane and an inside of the first chamber is maintained under predetermined environment conditions; and
the moving stage is moved within a range where the introduction port of the first plane is positioned within the opening of the first chamber,
wherein the first plane includes an opening/shutting unit that enables the first plane to be partially opened and shut, and wherein the opening/shutting unit enables switching between a first state in which the first chamber is exposed to the external space through an opening of the first plane, a second state in which the opening of the first plane is closed, and a third state in which illumination light is introduced into the first chamber through a transparent window member.

2. The environment holding apparatus according to claim 1, wherein the predetermined conditions of the gas include at least one of temperature, humidity, and composition.

3. The environment holding apparatus according to claim 2, wherein the composition of the gas includes air and carbon dioxide gas.

4. The environment holding apparatus according to claim 1, wherein the opening/shutting unit enables switching between a first state in which the first chamber is exposed to an external space through an opening of the first plane and a second state in which the opening of the first plane is closed.

5. The environment holding apparatus according to claim 1, further comprising a second chamber that stores the first chamber and the moving stage, wherein the first plane forms one of an exterior group of planes of the second chamber.

6. The environment holding apparatus according to claim 5, wherein the first chamber includes a first opening and a shutter having a function of opening/shutting the first opening; and the second chamber includes a second opening and a shutter, which has a function of opening/shutting the second opening, at a position facing the first opening.

7. An environment control type analyzer, comprising:
an environment holding apparatus according to claim 1;
an analyzer that analyzes a sample held within the first chamber; and
an environment adjustment apparatus that is connected to the first chamber through the pipe and the first plane to maintain the inside of the first chamber under a predetermined environment.

8. An environment control type analyzer comprising:
an environment holding apparatus according to claim 1;
an analyzer that analyzes a sample held within the first chamber;
a transmitted illumination device that is provided to face a detecting unit of the analyzer with the sample put therebetween, and that illuminates the sample through a window member; and
an environment adjustment apparatus that is connected to the first chamber through the pipe and the first plane to maintain the inside of the first chamber under a predetermined environment.

9. An environment control type analyzer comprising:
an environment holding apparatus according to claim 5;
an analyzer at least a part of which is disposed within the second chamber, and that analyzes a sample held within the first chamber; and
an environment adjustment apparatus that is connected to the first chamber through the pipe and the first plane to maintain the inside of the first chamber under a predetermined environment.

10. The environment control type analyzer according to claim 9, further comprising a dehumidifier that dehumidifies the inside of the second chamber.

11. An environmental control type analyzer, comprising:
an environmental holding apparatus according to claim 1;
a microscope that is provided outside of the first chamber and with which the sample held within the first chamber is observed.

12. The environmental control type analyzer according to claim 11, wherein;
the first plane includes an opening/shutting unit that enables the first plane to be partially opened and shut, and enables switching between a first state in which the first chamber is exposed to the external space through an opening of the first plane and a second state in which the opening of the first plane is closed; and
the opening of the first plane is located on an optical axis of an objective lens of the microscope.

13. An environmental control type analyzer, comprising:
an environmental holding apparatus according to claim 1, wherein;
the first plane includes an opening/shutting unit that enables the first plane to be partially opened and shut, and enables switching between a first state in which the first chamber is exposed to the external space through an opening of the first plane and a second state in which the opening of the first plane is closed; and
an injector that is located to face the opening/shutting unit and enables injection of liquid onto the sample held within the first chamber.

* * * * *